United States Patent
Natsoulis et al.

(10) Patent No.: US 6,365,403 B1
(45) Date of Patent: *Apr. 2, 2002

(54) HIGH-EFFICIENCY AAV HELPER FUNCTIONS

(75) Inventors: Georges Natsoulis, San Francisco, CA (US); Gary Kurtzman, Villanova, PA (US); Peter Colosi, Alameda, CA (US)

(73) Assignee: Avigen, Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/449,581

(22) Filed: Nov. 29, 1999

Related U.S. Application Data (63) Continuation of application No. 09/107,708, filed on Jun. 30, 1998, now Pat. No. 6,027,931, which is a continuation-in-part of application No. 08/688,648, filed on Jul. 29, 1996, now abandoned, which is a continuation-in-part of application No. 08/510,790, filed on Aug. 3, 1995, now Pat. No. 5,622,856.

(51) Int. Cl.⁷ ............................ C12N 5/10; C07H 21/00
(52) U.S. Cl. .................... 435/325; 435/369; 435/366; 536/23.1; 536/23.72; 536/24.1
(58) Field of Search .................... 435/235.1, 320.1, 435/325, 348, 366, 367, 369; 536/23.1, 23.72, 24.1

(56) References Cited

U.S. PATENT DOCUMENTS

| | | | |
|---|---|---|---|
| 4,797,368 A | 1/1989 | Carter et al. ............. | 435/320.1 |
| 5,589,377 A | 12/1996 | Lebkowski et al. ......... | 435/369 |
| 5,622,856 A | 4/1997 | Natsoulis .................. | 435/325 |
| 5,658,776 A | 8/1997 | Flotte et al. ................ | 435/457 |
| 5,693,531 A | 12/1997 | Chiorini et al. ............. | 435/325 |
| 6,001,650 A | * 12/1999 | Colosi ......................... | 435/369 |
| 6,027,931 A | * 2/2000 | Natsoulis et al. ......... | 435/235.1 |

OTHER PUBLICATIONS

Li et al., "Role for Highly Regulated rep Gene Expression in Adeno–Associated Virus Vector Production," *Journal of Virology* 71(7):5236–5243 (1997).

Ogasawara et al., "The Use of Heterologous Promoters for Adeno–Associated Virus (AAV) Protein Expression in AAV Vector Production," *Microbiol. Immunol.* 42(3):177–185 (1998).

Vincent et al., "Analysis of Recombinant Adeno–Associated Virus Packaging and Requirements for rep and cap Gene Products," *Journal of Virology* 71(3):1897–1905 (1997).

* cited by examiner

Primary Examiner—Robert A. Schwartzman
(74) Attorney, Agent, or Firm—Robins & Pasternak LLP (57) ABSTRACT

The present invention provides methods and compositions for producing high titer preparations of recombinant AAV ("rAAV") virions. The compositions of the present invention include AAV helper function systems and host cells. The present invention also includes methods of using AAV helper function vectors that effect the production of only small amounts of the long forms of Rep protein, and rAAV virions produced by such methods.

13 Claims, 2 Drawing Sheets

SEQUENCE LISTING

<160> NUMBER OF SEQ ID NOS: 8

<210> SEQ ID NO 1
<211> LENGTH: 5
<212> TYPE: DNA
<213> ORGANISM: adeno-associated virus 2

<400> SEQUENCE: 1 ccgcc                                                                    5

<210> SEQ ID NO 2
<211> LENGTH: 5
<212> TYPE: DNA
<213> ORGANISM: Artificial Sequence
<220> FEATURE:
<223> OTHER INFORMATION: Description of Artificial Sequence:artificial
      sequence

<400> SEQUENCE: 2 aaaaa                                                                    5

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
gaacgcgcag aaaaaatgcc ggg                                               23

<210> SEQ ID NO 4
<211> LENGTH: 6
<212> TYPE: DNA
<213> ORGANISM: adeno-associated virus 2

<400> SEQUENCE: 4 cgcacg                                                                   6

<210> SEQ ID NO 5
<211> LENGTH: 6
<212> TYPE: DNA
<213> ORGANISM: Artificial Sequence
<220> FEATURE:
<223> OTHER INFORMATION: Description of Artificial Sequence:artificial
      sequence

<400> SEQUENCE: 5 aataaa                                                                   6

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
ggtttgaacg aataaacgcc atgc                                              24

<210> SEQ ID NO 7
<211> LENGTH: 24

```
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
ggtttgaacg agcgctcgcc atgc                                            24

<210> SEQ ID NO 8
<211> LENGTH: 48
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
aataaaggaa atttattttc attgcaatag tgtgttggtt ttttgtgt                  48
```

HIGH-EFFICIENCY AAV HELPER FUNCTIONS

RELATED APPLICATIONS

This application is a continuation of U.S. patent application Ser. No. 09/107,708, filed Jun. 30, 1998, issued as U.S. Pat. No. 6,027,931, which is a continuation-in-part of U.S. patent application Ser. No. 08/688,648, filed Jul. 29, 1996, now abandoned, which is a continuation-in-part of U.S. patent application Ser. No. 08/510,790, filed Aug. 3, 1995, issued as U.S. Pat. No. 5,622,856, from which applications priority is claimed pursuant to 35 U.S.C. §120, and which applications are incorporated herein by reference.

FIELD OF THE INVENTION

The present invention relates to adeno-associated virus (AAV) helper function systems for use in recombinant AAV (rAAV) virion production and methods of using such systems. More specifically, the present invention relates to AAV helper functions that produce low amounts of the long form of AAV Rep proteins, resulting in high-efficiency production of rAAV.

TECHNICAL BACKGROUND

Gene Therapy

Scientists are continually discovering genes that are associated with human diseases such as diabetes, hemophilia and cancer. Research efforts have also uncovered genes, such as erythropoietin (which increases red blood cell production), that are not associated with genetic disorders but code for proteins that can be used to treat numerous diseases. However, despite significant progress in the effort to identify and isolate genes, a major obstacle facing the biopharmaceutical industry is how to safely and persistently deliver effective quantities of these genes' products to patients.

Currently, the protein products of these genes are synthesized in cultured bacterial, yeast, insect, mammalian, or other cells and delivered to patients by intravenous injection. Intravenous injection of recombinant proteins has been successful but suffers from several drawbacks. First, patients frequently require multiple injections in a single day in order to maintain the necessary levels of the protein in the blood stream. Even then, the concentration of protein is not maintained at physiological levels—the level of the protein is usually abnormally high immediately following injection and far below optimal levels prior to injection. Second, intravenous delivery often cannot deliver the protein to the target cells, tissues or organs in the body. And, if the protein reaches its target, it is often diluted to non-therapeutic levels. Third, the method is inconvenient and severely restricts the patient's lifestyle. The adverse impact on lifestyle is especially significant when the patient is a child.

These shortcomings have led to the development of gene therapy methods for delivering sustained levels of specific proteins into patients. These methods allow clinicians to introduce DNA coding for a gene of interest directly into a patient (in vivo gene therapy) or into cells isolated from a patient or a donor (ex vivo gene therapy). The introduced DNA then directs the patient's own cells or grafted cells to produce the desired protein product. Gene delivery, therefore, obviates the need for daily injections. Gene therapy may also allow clinicians to select specific organs or cellular targets (e.g., muscle, blood cells, brain cells, etc.) for therapy.

DNA may be introduced into a patient's cells in several ways. There are transfection methods, including chemical methods such as calcium phosphate precipitation and liposome-mediated transfection, and physical methods such as electroporation. In general, transfection methods are not suitable for in vivo gene delivery. There are also methods that use recombinant viruses. Current viral-mediated gene delivery methods include retrovirus, adenovirus, herpes virus, pox virus, and adeno-associated virus (AAV) vectors. Of the more than 100 gene therapy trials conducted, more than 95% used viral-mediated gene delivery. C. P. Hodgson, *Bio/Technology* 13, 222–225 (1995).

Adeno-Associated Virus-Mediated Gene Therapy

One viral system that has been used for gene delivery is adeno-associated virus (AAV). AAV is a parvovirus which belongs to the genus Dependovirus. AAV has several attractive features not found in other viruses. First, AAV can infect a wide range of host cells, including non-dividing cells. Second, AAV can infect cells from different species. Third, AAV has not been associated with any human or animal disease and does not appear to alter the biological properties of the host cell upon integration. Indeed, it is estimated that 80–85% of the human population has been exposed to the virus. Finally, AAV is stable at a wide range of physical and chemical conditions which lends itself to production, storage and transportation requirements.

The AAV genome is a linear, single-stranded DNA molecule containing 4681 nucleotides. The AAV genome generally comprises an internal non-repeating genome flanked on each end by inverted terminal repeats (ITRs). The ITRs are approximately 145 base pairs (bp) in length. The ITRs have multiple functions, including as origins of DNA replication and as packaging signals for the viral genome.

The internal non-repeated portion of the genome includes two large open reading frames, known as the AAV replication (rep) and capsid (cap) genes. The rep and cap genes code for viral proteins that allow the virus to replicate and package the viral genome into a virion. In particular, a family of at least four viral proteins are expressed from the AAV rep region, Rep 78, Rep 68, Rep 52, and Rep 40, named according to their apparent molecular weight. The AAV cap region encodes at least three proteins, VP1, VP2, and VP3.

AAV is a helper-dependent virus; that is, it requires co-infection with a helper virus (e.g., adenovirus, herpesvirus or vaccinia) in order to form AAV virions. In the absence of co-infection with a helper virus, AAV establishes a latent state in which the viral genome inserts into a host cell chromosome, but infectious virions are not produced. Subsequent infection by a helper virus "rescues" the integrated genome, allowing it to replicate and package its genome into infectious AAV virions. While AAV can infect cells from different species, the helper virus must be of the same species as the host cell. Thus, for example, human AAV will replicate in canine cells co-infected with a canine adenovirus.

AAV has been engineered to deliver genes of interest by deleting the internal non-repeating portion of the AAV genome and inserting a heterologous gene between the ITRs. The heterologous gene is typically functionally linked to a heterologous promoter (constitutive, cell-specific, or inducible) capable of driving gene expression in the patient's target cells under appropriate conditions. Termination signals, such as polyadenylation sites, can also be included.

To produce infectious rAAV containing the heterologous gene, a suitable producer cell line is transfected with an AAV vector containing a heterologous gene. AAV helper functions and accessory functions, which are typically derived from a helper virus such as adenovirus, are then expressed in the producer cell. Once these factors come together, the heterologous gene is replicated and packaged as though it were a wild-type AAV genome, forming a recombinant virion. When a patient's cells are infected with the resulting rAAV virions, the heterologous gene enters and is expressed in the patient's cells. Because the patient's cells lack the rep and cap genes and the adenovirus accessory function genes, the rAAV are replication defective; that is, they cannot further replicate and package their genomes. Similarly, without a source of rep and cap genes, wild-type AAV cannot be formed in the patient's cells.

Methods of Producing rAAV

In the earliest attempts to generate rAAV virions, researchers cotransfected an AAV vector carrying heterologous DNA with a wild-type AAV genome. Alternatively, cells transfected with an AAV vector were infected with wild-type AAV particles. In both types of protocols, accessory functions were provided by infection with a helper virus such as adenovirus. The wild-type AAV genome provides the necessary rep and cap functions, but significant amounts of wild-type AAV are produced by these methods. Moreover, the rAAV titers produced are usually not sufficient for therapy.

In order to increase viral titers, several groups have focused their attention on Rep protein expression. For example, one group of researchers constructed a plasmid containing the rep and cap genes linked to an SV40 origin of replication. See, e.g., U.S. Pat. No. 5,693,531. The SV40 origin of replication allows high copy number episomal replication of the plasmid in cells that express SV40 large T antigen. As a result, large amounts of Rep and Cap gene products are produced.

Many other researchers have replaced the AAV p5 promoter with heterologous promoters and enhancers in an effort to increase rAAV titers. For example, one group of researchers replaced the p5 promoter with the HIV LTR. U.S. Pat. No. 5,658,776. In 293 cells, which express the adenoviral E1A gene product, the HIV LTR provides strong constitutive expression of the Rep gene products. The authors emphasize that use of the HIV LTR avoids the problem of Rep autoregulating expression from the p5 promoter, and conclude that in previously used methods, levels of Rep expression are limiting in the production of rAAV.

All of these approaches reflect a widely held notion that expressing large amounts of the Rep gene products will allow the production of high titer rAAV. The long forms of Rep, however, have toxic effects on many cell types.

From the foregoing, it will be appreciated that it would be an advancement in the art to provide AAV helper functions that allow high efficiency production of rAAV. It would be a further advancement in the art to provide such helper functions that produce only small quantities of the long forms of the Rep proteins.

Such AAV helper functions and methods of their use are disclosed herein.

BRIEF SUMMARY OF THE INVENTION

The present invention relates to AAV helper function systems for rAAV production and methods of using such systems. In certain embodiments, a method of the present invention includes the steps of (1) introducing an AAV vector into a suitable host cell; (2) introducing an AAV helper function vector into the host cell such that the host cell produces only small amounts of the long forms of Rep protein; (3) expressing accessory functions in the host cell; and (4) culturing the host cell to produce rAAV virions. In certain preferred embodiments, the amount of the long forms of Rep protein produced are substantially less than the amount that would be produced in the host cell using an AAV helper function vector expressing the long forms of Rep protein under the control of an AAV promoter. In certain other embodiments, the amount of the long forms of Rep protein produced are less than the quantities of the short forms of Rep protein produced by the host cell. It will be appreciated that both transcriptional and translational controls may be used to limit the levels of the long forms of Rep protein that are produced.

The AAV vector and AAV helper function vector can be transfected into the host cell, either sequentially or simultaneously, using well-known techniques. Accessory functions may be expressed in any of several ways, including infecting the host cell with a suitable helper virus (such as adenovirus, herpesvirus, or vaccinia virus), or by transfecting one or more accessory function vectors into the host cell. It is also well known in the art that certain cell lines, e.g., 293 cells, inherently express one or more accessory functions.

An AAV helper function vector of the present invention may be a plasmid, bacteriophage, transposon, cosmid, chromosome, artificial chromosome, virus, or other suitable genetic element, and may include selectable genetic markers such as antibiotic resistance genes. Such vectors may also include one or more accessory function genes, such as the E1A, E1B, E2A, VA RNA, and E4 regions of adenovirus.

Also provided herein are host cells for producing rAAV virions. In certain embodiments, a host cell of the present invention comprises an AAV helper function vector that directs the host cell to produce only small amounts of the long forms of Rep protein. Upon introduction of an AAV vector and expression of accessory functions in the host cell, rAAV virions are produced. In certain preferred embodiments, a host cell of the present invention also includes one or more accessory functions.

The rAAV virions produced using the present invention may be used to introduce genetic material into animals, including humans, or isolated animal cells for a variety of research and therapeutic uses. For example, rAAV virions produced using the methods of the present invention may be used to express a protein in animals to gather preclinical data or to screen for potential drug candidates. Alternatively, the rAAV virions may be used to transfer genetic material into a human to cure a genetic defect or to effect a desired treatment.

These and other objects and advantages of the present invention will become apparent upon reference to the accompanying drawing and upon reading the following detailed description and appended claims.

DETAILED DESCRIPTION OF THE INVENTION

The present invention is directed to novel systems and methods for producing rAAV for introducing genetic material into animals or animal cells for a variety of research and therapeutic uses. A physician or researcher may wish to introduce DNA into an organism (or cells isolated from an organism) for any of several reasons. First, DNA may be introduced to correct a defective gene. Second, DNA may be introduced to specifically delete or mutate a given gene by, for example, homologous recombination. Third, DNA may be introduced to express a protein. Such a protein may be expressed to achieve a therapeutic benefit within the organism treated with rAAV. Alternatively, a protein may be expressed in an organism or in cells isolated from an organism with the goal of isolating and purifying the protein product. Unlike previously described methods for producing rAAV, however, the methods of the present invention utilize AAV helper function vectors that effect the production of only low levels of the long forms of Rep protein, while generating high titer stocks of rAAV.

All publications, patents, and patent applications cited herein are hereby incorporated by reference.

Definitions

In describing the present invention, the following terms will be employed, and are intended to be defined as indicated below.

"Gene transfer" or "gene delivery" refers to methods or systems for reliably inserting foreign DNA into host cells. Gene transfer can result in transient expression of non-integrated transferred DNA, extrachromosomal replication and expression of transferred replicons (e.g., episomes), or integration of transferred genetic material into the genomic DNA of host cells. Gene transfer provides a unique approach for the treatment of acquired and inherited diseases. A number of systems have been developed for gene transfer into mammalian cells. See, e.g., U.S. Pat. No. 5,399,346.

By "vector" is meant any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors.

By "adeno-associated virus inverted terminal repeats" or "AAV ITRs" is meant the art-recognized regions found at each end of the AAV genome which function together in cis as origins of DNA replication and as packaging signals for the viral genome. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. See, e.g., Kotin, R. M. (1994) Human Gene Therapy 5, 793–801; Berns, K. I. "Parvoviridae and their Replication" in Fundamental Virology, 2d ed., (B. N. Fields and D. M. Knipe, eds.) for the AAV-2 sequence. As used herein, an "AAV ITR" need not have the wild-type nucleotide sequence depicted in these references, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

By "AAV rep coding region" is meant the art-recognized region of the AAV genome which encodes the replication proteins of the virus which are required to replicate the viral genome and to insert the viral genome into a host genome during latent infection. The term also includes functional homologues thereof such as the human herpesvirus 6 (HHV-6) rep gene which is also known to mediate AAV-2 DNA replication (Thomson et al. (1994) Virology 204, 304–311). For a further description of the AAV rep coding region, see, e.g., Muzyczka, N. (1992) Current Topics in Microbiol. and Immunol. 158, 97–129; Kotin, R. M. (1994) Human Gene Therapy 5, 793–801. The rep coding region, as used herein, can be derived from any viral serotype, such as the AAV serotypes described above. The region need not include all of the wild-type genes but may be altered, e.g., by the insertion, deletion or substitution of nucleotides, so long as the rep genes present provide for sufficient integration functions when expressed in a suitable recipient cell.

The terms "long forms of Rep protein" and "large Rep" refer to the Rep 78 and Rep 68 gene products of the AAV rep coding region, including functional homologues thereof. The long forms of Rep are normally expressed under the direction of the AAV p5 promoter, which has been described and characterized.

The terms "short forms of Rep protein" and "small Rep" refer to the Rep 52 and Rep 40 gene products of the AAV rep coding region, including functional homologues thereof. The short forms of Rep are expressed under the direction of the AAV p19 promoter, which has been described and characterized.

By "AAV cap coding region" is meant the art-recognized region of the AAV genome which encodes the coat proteins of the virus which are required for packaging the viral genome. For a further description of the cap coding region, see, e.g., Muzyczka, N. (1992) Current Topics in Microbiol. and Immunol. 158, 97–129; Kotin, R. M. (1994) Human Gene Therapy 5, 793–801. The AAV cap coding region, as used herein, can be derived from any AAV serotype, as described above. The region need not include all of the wild-type cap genes but may be altered, e.g., by the insertion, deletion or substitution of nucleotides, so long as the genes provide for sufficient packaging functions when present in a host cell along with an AAV vector.

The term "AAV coding region" refers to a nucleic acid molecule that includes the two major AAV open reading frames corresponding to the AAV rep and cap coding regions; e.g., a nucleic acid molecule comprising a nucleotide sequence substantially homologous to base pairs 310 through 4,440 of the wild-type AAV genome. Thus, for purposes of the present invention, an AAV coding region does not include those sequences corresponding to the AAV p5 promoter region, and does not include the AAV ITRs.

By an "AAV vector" is meant a vector derived from an adeno-associated virus serotype, including without limitation, AAV-1, AAV-2, AAV-3, AAV-4, AAV-5, AAVX7, etc. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging.

"AAV helper functions" refer to AAV-derived coding sequences that can be expressed to provide AAV gene products that, in turn, function in trans for productive AAV replication. Thus, AAV helper functions include the rep and cap regions. The rep expression products have been shown to possess many functions, including, among others: recognition, binding and nicking of the AAV origin of DNA replication; DNA helicase activity; and modulation of transcription from AAV (or other heterologous) promoters. The cap expression products supply necessary packaging functions. AAV helper functions are used herein to complement AAV functions in trans that are missing from AAV vectors.

The term "AAV helper construct" refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for lytic AAV replication; however, helper constructs lack AAV ITRs and can neither replicate nor package themselves. AAV helper constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) *J. Virology* 63, 3822–3828; McCarty et al. (1991) *J. Virology* 65, 2936–2945. A number of other vectors have been described which encode Rep and/or Cap expression products. See, e.g., U.S. Pat. No. 5,139,941.

The term "accessory functions" refers to non-AAV derived viral and/or cellular functions upon which AAV is dependent for its replication. Thus, the term captures DNAs, RNAs and proteins that are required for AAV replication, including those moieties involved in activation of AAV gene transcription, stage specific AAV mRNA splicing, AAV DNA replication, synthesis of Cap expression products and AAV capsid assembly. Viral-based accessory functions can be derived from any of the known helper viruses such as adenovirus, herpesvirus (other than herpes simplex virus type-1) and vaccinia virus.

For example, adenovirus-derived accessory functions have been widely studied, and a number of adenovirus genes involved in accessory functions have been identified and partially characterized. See, e.g., Carter, B. J. (1990) "Adeno-Associated Virus Helper Functions," in *CRC Handbook of Parvoviruses*, vol. I (P. Tijssen, ed.); Muzyczka, N. (1992) *Current Topics. Microbiol. and Immun.* 158, 97–129. Specifically, early adenoviral E1A, E2A, E4, VA RNA and, possibly, E1B regions are thought to participate in the accessory process. Janik et al. (1981) *Proc. Natl. Acad. Sci. USA* 78, 1925–1929. Herpesvirus-derived accessory functions have been described. See, e.g., Young et al. (1979) *Prog. Med. Virol.* 25, 113. Vaccinia virus-derived accessory functions have also been described. See, e.g.,Carter, B. J. (1990), supra., Schlehofer et al. (1986) *Virology* 152, 110–117.

The term "accessory function vector" refers generally to a nucleic acid molecule that includes nucleotide sequences providing accessory functions. An accessory function vector can be transfected into a suitable host cell, wherein the vector is then capable of supporting AAV virion production in the host cell. Expressly excluded from the term are infectious viral particles as they exist in nature, such as adenovirus, herpesvirus or vaccinia virus particles. Thus, accessory function vectors can be in the form of a plasmid, phage, transposon, cosmid or virus that has been modified from its naturally occurring form.

By "recombinant virus" is meant a virus that has been genetically altered, e.g., by the addition or insertion of a heterologous nucleic acid construct into the particle.

By "AAV virion" is meant a complete virus particle, such as a wild-type (wt) AAV virus particle (comprising a linear, single-stranded AAV nucleic acid genome associated with an AAV capsid protein coat). In this regard, single-stranded AAV nucleic acid molecules of either complementary sense, i.e., "sense" or "antisense" strands, can be packaged into any one AAV virion and both strands are equally infectious.

A "recombinant AAV virion," or "rAAV virion" is defined herein as an infectious, replication-defective virus composed of an AAV protein shell encapsulating a heterologous nucleotide sequence of interest that is flanked on both sides by AAV ITRs. A rAAV virion is produced in a suitable host cell comprising an AAV vector, AAV helper functions, and accessory functions. In this manner, the host cell is rendered capable of encoding AAV polypeptides that are required for packaging the AAV vector (containing a recombinant nucleotide sequence of interest) into infectious recombinant virion particles for subsequent gene delivery.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) *Virology*, 52, 456; Sambrook et al. (1989) *Molecular Cloning A Laboratory Manual*, Cold Spring Harbor Laboratories, New York; Davis et al. (1986) *Basic Methods in Molecular Biology*, Elsevier; Chu et al. (1981) *Gene* 13, 197. Such techniques can be used to introduce one or more exogenous DNA moieties, such as a nucleotide integration vector and other nucleic acid molecules, into suitable host cells.

The term "host cell" denotes, for example, microorganisms, yeast cells, insect cells, and mammalian cells, that can be, or have been, used as recipients of an AAV helper construct, an AAV vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement to the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "coding sequence" or a sequence which "encodes" a particular protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic MRNA, genomic DNA sequences from prokaryotic or eukaryotic DNA, and even synthetic DNA sequences. A transcription termination sequence will usually be located 3' to the coding sequence.

A "nucleic acid" sequence refers to a DNA or RNA sequence. The term captures sequences that include any of the known base analogues of DNA and RNA such as, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, 2-thiocytosine, and 2,6-diaminopurine.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter region" is used herein in its ordinary sense to refer to a DNA regulatory sequence to which RNA polymerase binds, initiating transcription of a downstream (3' direction) coding sequence.

An "AAV p5 promoter region" encompasses both promoter sequences with identity to a p5 promoter region isolated from an AAV serotype, including without limitation, AAV-1, AAV-2, AAV-3, AAV-4, AAV-5, AAVX7, etc., as well as those that are substantially homologous and functionally equivalent thereto. The AAV p5 promoter directs the expression of the long forms of Rep, and has been described and characterized.

The phrase "substantially less than an amount produced from an AAV helper function vector expressing the long forms of Rep protein under control of an AAV p5 promoter" refers to a comparison between an AAV helper function vector of interest and an AAV helper function vector in which the expression of the long forms of Rep protein is directed by an AAV p5 promoter, e.g., the commonly used plasmids pAAV/Ad and pIM29+45. The phrase implies a comparison under equivalent conditions in equivalent host cells. Techniques for conducting such a comparison are well known in the art, and include RNA analytical methods, e.g., Northern blotting, and protein analytical methods, e.g., Western blotting. An AAV helper function vector of interest causes a host cell to produce an amount of the long forms of Rep protein that is substantially less than an amount produced from an AAV helper function vector expressing the long forms of Rep protein under control of an AAV p5 promoter when the amount of the long forms of Rep protein produced by the vector of interest are less than 20%, more preferably less than 10%, and most preferably less than 5%, of the amount produced by the vector in which large Rep expression is driven by the p5 promoter.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

By "isolated," when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "3'," or "5'" relative to another sequence, it is to be understood that it is the position of the sequences in the "sense" or "coding" strand of a DNA molecule that is being referred to, as is conventional in the art.

"Homology" refers to the percent of identity between two polynucleotide or two polypeptide moieties. The correspondence between the sequence from one moiety to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which allow for the formation of stable duplexes between homologous regions, followed by digestion with singlestranded-specific nuclease(s), and size determination of the digested fragments. Two DNA or two polypeptide sequences are "substantially homologous" to each other when at least about 80%, preferably at least about 90%, and most preferably at least about 95% of the nucleotides or amino acids match over a defined length of the molecules, as determined using the methods above.

A "functional homologue" or a "functional equivalent" of a given polypeptide includes molecules derived from the native polypeptide sequence, as well as recombinantly produced or chemically synthesized polypeptides which function in a manner similar to the reference molecule to achieve a desired result. Thus, a functional homologue of AAV Rep68 or Rep78 encompasses derivatives and analogues of those polypeptides, including any single or multiple amino acid additions, substitutions and/or deletions occurring internally or at the amino or carboxy termini thereof—so long as integration activity remains.

A "functional homologue" or a "functional equivalent" of a given adenoviral nucleotide region includes similar regions derived from a heterologous adenovirus serotype, nucleotide regions derived from another virus or from a cellular source, and recombinantly produced or chemically synthesized polynucleotides which function in a manner similar to the reference nucleotide region to achieve a desired result. Thus, a functional homologue of an adenoviral VA RNA gene region or an adenoviral E2A gene region encompasses derivatives and analogues of such gene regions-including any single or multiple nucleotide base additions, substitutions and/or deletions occurring within the regions, so long as the homologue retains the ability to provide its inherent accessory function to support AAV virion production at levels detectable above background.

General Methods

It is a primary object of the present invention to provide improved AAV helper function systems, host cells, and methods of their use for the production of rAAV virions. More particularly, it is an object of the present invention to provide AAV helper function systems, host cells, and methods that support high-efficiency rAAV production by producing only small amounts of the long forms of Rep protein.

In certain embodiments, a method of the present invention includes the steps of (1) introducing an AAV vector into a suitable host cell; (2) introducing an AAV helper function vector into the host cell such that the host cell produces only small amounts of the long forms of Rep protein; (3) expressing accessory functions in the host cell; and (4) culturing the host cell to produce rAAV virions. In certain preferred embodiments, the amount of the long forms of Rep protein produced is substantially less than the amount that would be produced in an equivalent host cell using an AAV helper function vector expressing the long forms of Rep protein under the control of an AAV promoter. The relative amounts of Rep proteins produced may be compared using techniques that are well known in the art, including immunochemical techniques such as Western blotting, immunoprecipitation, immunoaffinity purification, and immunofluorescence. These immunochemical techniques utilize anti-Rep antibodies, which are commercially available, e.g., Mab226.7 from American Research Products (Belmont, Mass.).

In certain other embodiments, the amount of the long forms of Rep protein produced are less than the quantities of the short forms of Rep protein produced by the host cell. The relative amounts of the long and short forms of Rep proteins produced may be compared by the techniques listed above.

It will be appreciated that both transcriptional and translational controls may be used to limit the levels of the long forms of Rep protein that are produced. Transcriptional controls include the use of heterologous promoter and enhancer sequences such as inducible promoters that attenuate the expression of the long forms of Rep protein. The effects of transcriptional regulation may be assayed by techniques that are well known in the art, including Northern blotting of host cell total RNA or mRNA. The effects of transcriptional control may also be assayed by determining the effect on Rep protein concentration using the techniques listed above.

An AAV helper function vector that contains rep and cap sequences with wild-type promoter and gene configurations may be used to determine baseline levels of the production of Rep isoforms and expression of rAAV. A modified vector that effects decreased expression of the long forms of Rep protein and increased expression of the short forms of Rep protein shows increases in rAAV virion production relative to such a wild-type construct. In fact, we show that contrary to conventional wisdom, expression of the long forms of Rep protein is inversely proportional to rAAV virion production. By contrast, expression of the short forms of Rep protein was directly proportional to rAAV virion production.

Relocation of the p5 promoter to the 3' end of the cap gene (pW1909) resulted in the lowest expression of the long forms of Rep protein, the highest expression of the short forms of Rep protein, and the highest production of recombinant virions. Introduction of an efficient polyadenylation site (pRCM.globinpolyA) between the transcriptional start site and the first codon in the coding sequence of the long forms of Rep protein also decreased expression of the long forms of Rep and increased expression of the short forms of Rep protein, but less so. Consequently, recombinant virion production was improved relative to the wild-type constructs but was less than pW1909. Modification of the Kozak sequence so as to reduce translation initiation efficiency (pRCM.kozak) and introduction of a sub-optimal polyadenylation site had little effect on Rep protein expression and resulted in little improvement in recombinant virion production.

In the methods of the present invention, an AAV vector and AAV helper function vector can be transfected into the host cell, either sequentially or simultaneously, using well-known techniques. These vectors can be readily introduced into a suitable host cell using transfection techniques that are known in the art. Such transfection methods have been described, including calcium phosphate co-precipitation (Graham et al. (1973) Virol. 52:456–467), direct microinjection into cultured cells (M. R. Capecchi (1980) Cell 22:479–488), electroporation (Shigekawa et al. (1988) BioTechniques 6:742–751), liposome-mediated gene transfer (Mannino et al. (1988) BioTechniques 6:682–690), lipid-mediated transfection (Felgner et al. (1987) Proc. NatL. Acad. Sci. USA 84:7413–7417), and nucleic acid delivery using high-velocity microprojectiles (Klein et al. (1987) Nature 327:70–73).

AAV helper function vectors can be engineered using conventional recombinant techniques. Particularly, nucleic acid molecules can be readily assembled in any desired order by inserting one or more accessory function nucleotide sequences into a construct, such as by ligating restriction fragments or PCR-generated products into a cloning vector using polylinker oligonucleotides or the like. The newly formed nucleic acid molecule can then be excised from the vector and placed in an appropriate expression construct using restriction enzymes or other techniques that are well known in the art.

More particularly, selected AAV nucleotide sequences or functional homologues thereof can be excised either from a viral genome or from a vector containing the same. Alternatively, selected AAV nucleotide sequences may be generated as PCR products using as a template either viral DNA or a vector containing such DNA. The nucleotide sequences are then inserted into a suitable vector either individually or linked together to provide a helper function construct using standard ligation techniques such as those described in Sambrook et al., supra.

Nucleic acid molecules comprising one or more helper functions can also be synthetically derived using a combination of solid phase direct oligonucleotide synthesis chemistry and enzymatic ligation methods that are conventional in the art. Synthetic sequences may be constructed having features such as restriction enzyme sites, and can be prepared in commercially available oligonucleotide synthesis devices such as those devices available from Applied Biosystems, Inc. (Foster City, Cailf.) using the phosphorarnidite method. See, e.g., Beaucage et al. (1981) *Tetrahedron Lett.* 22:1859–1862. Preferred codons for expression of the synthetic molecule in mammalian cells can also be readily synthesized. Complete nucleic acid molecules are then assembled from overlapping oligonucleotides prepared by the above methods. See, e.g., Edge, *Nature* 292, 756 (1981); Nambair et al., *Science* 223, 1299 (1984); Jay et al., *J Biol. Chem.* 259, 6311 (1984).

An AAV helper function vector utilized in the present invention may be a plasmid, bacteriophage, transposon, cosmid, chromosome, artificial chromosome, virus, or other suitable genetic element, and may include selectable genetic markers. Suitable markers include genes which confer antibiotic resistance or sensitivity, or impart color, or change the antigenic characteristics when cells which have been transfected with the nucleic acid constructs are grown in an appropriate selective medium. Particular selectable marker genes useful in the practice of the invention include the Neomycin resistance gene (encoding Aminoglycoside phosphotranferase (APH)) that allows selection in mammalian cells by conferring resistance to G418 (available from Sigma, St. Louis, Mo.) and the Hygromycin-B resistance gene (encoding Hygromycin-B-phosphotransferase (HPH)) that confers resistance to Hygrogmycin-B. Other suitable markers are known to those of skill in the art.

Such vectors can further include elements that control the replication and expression of the nucleic acid sequences that code for one or more AAV helper functions.

Accessory functions may be expressed in any of several ways, including infecting the host cell with a suitable helper virus (such as adenovirus, herpesvirus, or vaccinia virus), or by transfecting one or more accessory function vectors into the host cell. An AAV helper function vector may also include one or more accessory function genes, such as those derived from adenovirus, and may include one or more of the adenoviral E1A, E1B, E2A, VA RNA, and E4 regions.

Also provided herein are host cells for producing rAAV virions. In certain embodiments, a host cell of the present invention comprises an AAV helper function vector that directs the host cell to produce only small amounts of the long forms of Rep protein. Upon introduction of an AAV vector and expression of accessory functions in the host cell, rAAV virions are produced. In certain preferred embodiments, a host cell of the present invention also includes one or more accessory functions.

An AAV vector, AAV helper function vector and accessory function vector(s) can be introduced into the host cell, either simultaneously or serially, using transfection techniques described above.

AAV vectors used to produce rAAV virions for delivery of a nucleotide sequence of interest can be constructed to include one or more heterologous nucleotide sequences flanked on both ends (5' and 3') with functional AAV ITRs. In the practice of the invention, an AAV vector generally includes at least one AAV ITR and an appropriate promoter sequence suitably positioned relative to a heterologous nucleotide sequence, and at least one AAV ITR positioned downstream of the heterologous sequence. The 5' and 3' ITRs need not necessarily be identical to, or derived from, the same AAV isolate, so long as they function as intended.

Suitable heterologous nucleotide sequences for use in AAV vectors include any functionally relevant nucleotide sequence. Thus, AAV vectors for use in the practice of the invention can include any desired gene that encodes a protein that is defective or missing from a recipient cell genome or that encodes a non-native protein having a desired biological or therapeutic effect (e.g., an antiviral function), or the sequence can correspond to a molecule having an antisense or ribozyme function.

AAV vectors can also include control sequences, such as promoter and polyadenylation sites, as well as selectable markers or reporter genes, enhancer sequences, and other control elements which allow for the induction of transcription. Such AAV vectors can be constructed using techniques well known in the art.

In the methods of the invention, accessory functions are used for rAAV production. Accessory functions may be provided by infecting the host cell with a suitable helper virus, such as adenovirus, herpesvirus, or vaccinia virus, or by transfecting the host cell with one or more accessory function vectors.

Materials and Methods

Figure 1:
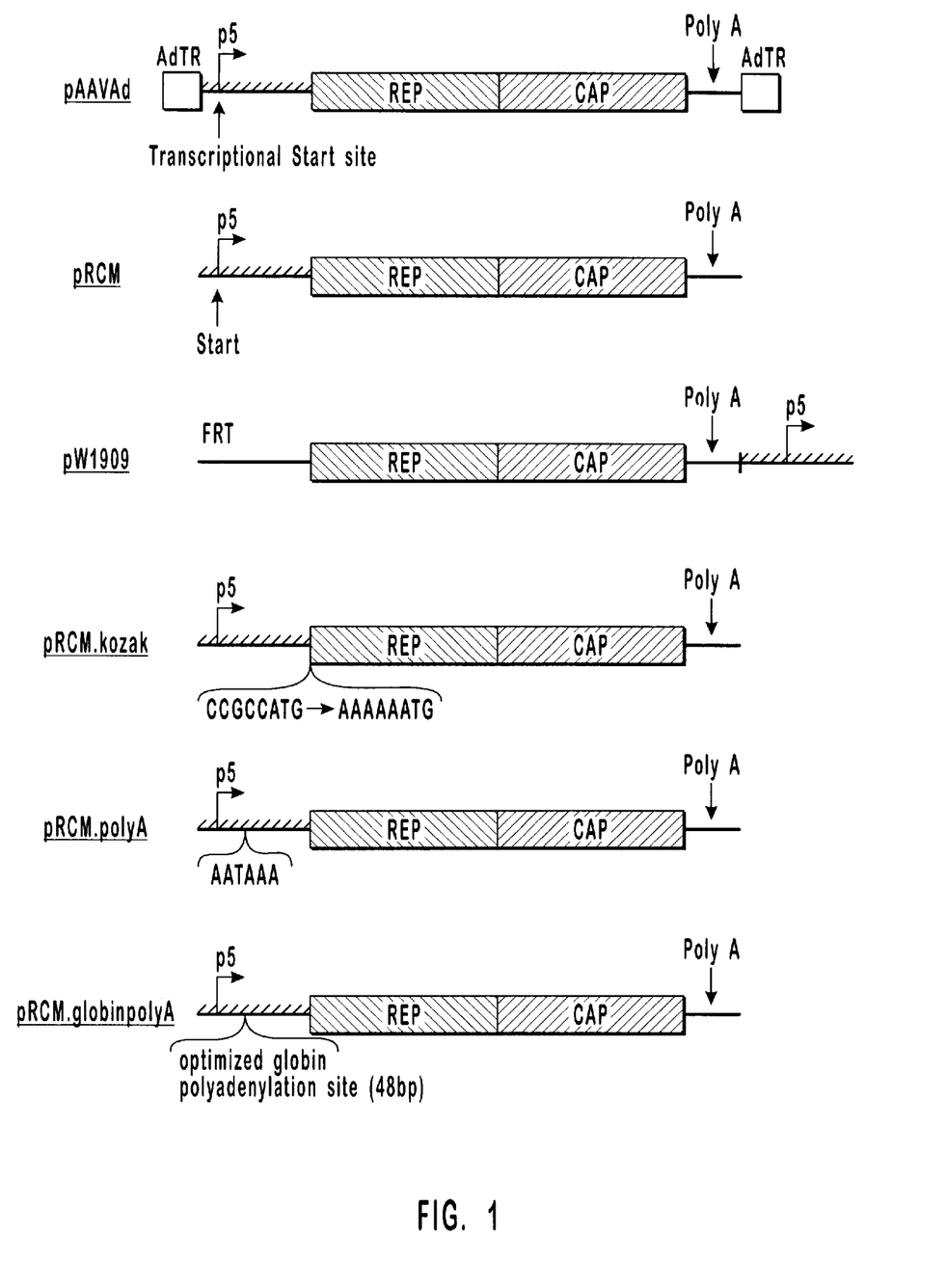
FIG. 1 depicts the promoter, rep, and cap configurations of a number of AAV helper function vectors.

Plasmid pW1909 has previously been described. See U.S. patent application Ser. No. 08/688,648. Briefly, as shown in FIG. 1, pW1909 comprises rep and cap coding regions and a downstream p5 promoter sandwiched between two Flip Recombination Target (FRT) sites.

Plasmid pRCM is composed of a DNA fragment encoding the entire AAV genome without the ITR sequences (base pairs 146–4536) cloned into the Small site of pUC119. Plasmids pRCM.kozak, pRCM.polyA and pRCM.globin-polyA are modified versions of pRCM in which the 5' untranslated region between the transcriptional start site and the first codon of large Rep has been modified by the introduction of Kozak sequence alterations and polyadenylation sites. In pRCM.kozak, the five base pair sequence immediately preceding the first codon was changed from 5'-CCGCC-3' (SEQ ID NO:1) to 5'-AAAAA-3' (SEQ ID NO:2). This was done by oligonucleotide-directed mutagenesis using the following oligonucleotide: 5'-GAACGCGCAGAAAAAATGCCGGG-3' (SEQ ID NO:3). Plasmid pRCM.polyA was made by changing base pairs −10 through −5, relative to the first codon of large Rep, from 5'-CGCACG-3' (SEQ ID NO:4) to 5'-AATAAA-3' (SEQ ID NO:5) using the following oligonucleotide: 5'-GGTTTGAACGAATAAACGCCATGC-3' (SEQ ID NO:6). Plasmid pRCM.globinpolyA was constructed by inserting a 48 bp fragment encoding an optimized polyadenylation site (based on the rabbit beta-globin polyadenylation site, Levitt et al. (1989), *Genes and Development* 3,1019–1025) between base pairs −8 and −7 relative to the start codon of large Rep. To do this, an Eco47III site was introduced in the 5' untranslated region using the primer 5'-GGTTTGAACGAGCGCTCGCCATGC-3' (SEQ ID NO:7). The resulting 7559 bp plasmid was called pUCRCM47III. Synthetic DNA encoding the polyadenylation site (5'-AATAAAGGAAATTTATTTTCATTGCAATAGTGTGTT-GGTTTTTTGTGT-3' (SEQ ID NO:8)) was inserted at this site.

EXAMPLES

The following examples are given to illustrate various embodiments which have been made within the scope of the present invention. It is to be understood that the following examples are neither comprehensive nor exhaustive of the many types of embodiments which can be prepared in accordance with the present invention.

Example 1

Western Blot 293 cells (available from ATCC, catalog number CRL-1573) in 10 cm dishes were transfected with 10 µg each of pVlacZ, pladeno5, and various AAV helper function constructs, which are depicted schematically in FIG. 1. Rep isoforms were analyzed by western blot analysis (shown in FIG. 2) using an anti-Rep monoclonal antibody.

AAVlacZ vector was produced and titer as previously described. Western blot analysis of the freeze/thaw lysates from vector production was carried out by standard methods using an 8% SDS polyacrylamide gel, electrotransfer to a nitrocellulose membrane, a monoclonal antibody to the AAV Rep protein (American Research Products, Belmont, Mass., Mab226.7) and chemiluminescent detection.

Figure 2:
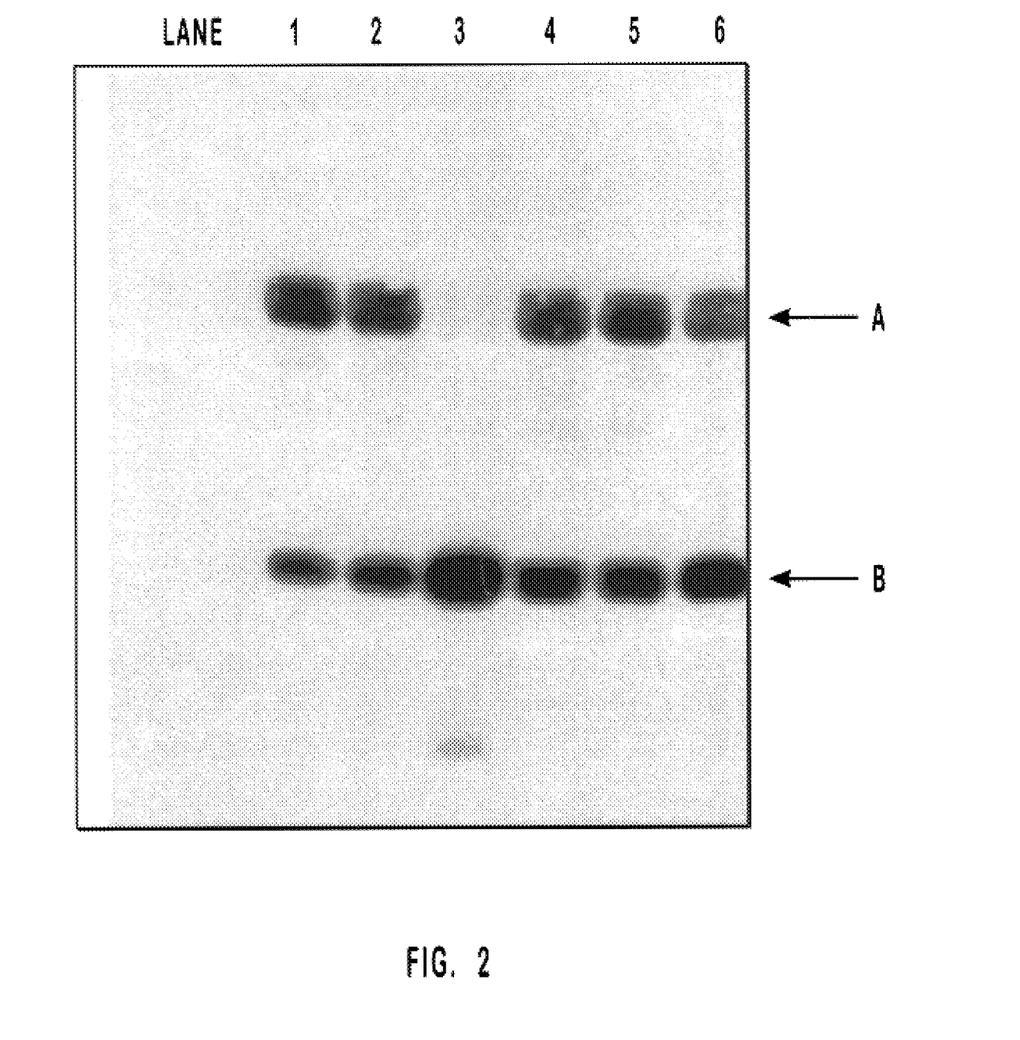
FIG. 2 illustrates a Western Blot of lysates from 293 cells transfected with various AAV helper function vectors and probed with anti-Rep antibody.

FIG. 2 illustrates a Western Blot of lysates prepared from 293 cells transfected with various AAV helper function vectors and probed with anti-Rep antibody. Lane 1 contains lysate from a cell transfected with the pAAVAd vector. Lane 2 contains lysate from a cell transfected with the pRCM vector. Lane 3 contains lysate from a cell transfected with the pW1909 vector. Lane 4 contains lysate from a cell transfected with the pRCM.kozak vector. Lane 5 contains lysate from a cell transfected with the pRCM.polyA vector. Lane 6 contains lysate from a cell transfected with the pRCM.globinpolyA. Arrow A indicates the position of the long forms of Rep protein, while Arrow B indicates the position of the short forms of Rep protein.

Lanes 1 and 2 (pAAVAd and pRCM, respectively) expressed similar amounts of both the long and short forms of Rep protein. By contrast, the cells transfected with pW1909 (lane 3) produced very little of the long forms of Rep. The cells transfected with pW1909 also produced more of the short forms of Rep than were produced by cells transfected with the other AAV helper function vectors. Modification of the Kozak sequence so as to reduce translation initiation efficiency (pRCM.kozak; lane 4) and introduction of a sub-optimal polyadenylation site between the transcriptional start site and the first codon in the coding sequence of the long forms of Rep protein (pRCM.polyA; lane 5) had little effect on Rep protein expression. Introduction of an efficient polyadenylation site (pRCM.globinpolyA; lane 6) between the transcriptional start site and the first codon in the coding sequence of the long forms of Rep protein also decreased expression of the long forms of Rep and increased expression of the short forms of Rep protein, but less so.

Example 2 rAAV Titers

AAVlacZ vector was produced by transfecting 293 cells in 10 cm dishes with 10 µg each of pVlacZ, pladeno5, and various rep and cap constructs, as described in Example 1, above. AAVlacZ virion preparations were titered on 293 cells in the presence of adenovirus. The results of the vector production are shown in the table below.

TABLE 1

| Helper Function Vector | AAVlacZ Titer/ 10 cm Plate | Relative Production |
| --- | --- | --- |
| pAAVAd | $7.3 \times 10^8$ | 0.85 |
| pRCM | $8.6 \times 10^8$ | 1.0 |
| pW1909 | $3.0 \times 10^9$ | 3.5 |
| pRCM.kozak | $9.0 \times 10^8$ | 1.05 |
| pRCM.polyA | $8.5 \times 10^8$ | 0.98 |
| pRCM.globinpolyA | $2.0 \times 10^9$ | 2.32 | pAAVAd and pRCM both contain rep and cap sequences with wild-type promoter and gene configurations. These plasmids produced similar amounts of AAVlacZ and expressed similar amounts of both the long and short forms of Rep protein. With the modified constructs, alterations that decreased expression of the long forms of Rep protein and increased expression of the short forms of Rep protein, relative to the wild-type constructs (pRCM and pAAVAd), also showed increases in AAVlacZ virion production relative to the wild-type constructs. In this series, expression of the long forms of Rep protein is inversely proportional to AAVlacZ virion production. By contrast, expression of the short forms of Rep protein was directly proportional to AAVlacZ virion production. Relocation of the p5 promoter to the 3' end of the cap gene (pW1909) resulted in the lowest expression of the long forms of Rep protein, the highest expression of the short forms of Rep protein, and the highest production of recombinant virions. Introduction of an efficient polyadenylation site (pRCM.globinpolyA) between the transcriptional start site and the first codon in the coding sequence of the long forms of Rep protein also decreased expression of the long forms of Rep and increased expression of the short forms of Rep protein, but less so. Consequently, recombinant virion production was improved relative to the pRCM but was less than pW1909. Modification of the Kozak sequence so as to reduce translation initiation efficiency (pRCM.kozak) and introduction of a sub-optimal polyadenylation site had little effect on Rep protein expression and resulted in little improvement in recombinant virion production.

In summary, the AAV helper function systems, host cells, and methods of the present invention allow for high-efficiency production of rAAV virions by reducing the amount of the long forms of Rep proteins produced. Here, we show that AAV helper function vectors that produce only small amounts of the long forms of Rep protein provide for higher titer rAAV virion production.

The invention may be embodied in other specific forms without departing from its essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

We claim:

1. A host cell comprising an AAV rep coding region, wherein the rep coding region comprises a nucleotide sequence that codes for long forms of Rep protein and short forms of Rep protein, wherein the host cell produces greater quantities of the short forms of Rep protein than of the long forms of Rep protein.

2. The host cell of claim 1, wherein the host cell further comprises an AAV cap coding region.

3. A host cell comprising an AAV rep coding region, wherein the rep coding region comprises a nucleotide sequence that codes for long forms of Rep protein and short forms of Rep protein, wherein the host cell produces substantially less of the long forms of Rep protein than of the short forms of Rep protein.

4. The host cell of claim 3, wherein the host cell further comprises an AAV cap coding region.

5. A host cell comprising an AAV helper function vector, wherein said AAV helper function vector comprises:

(a) an AAV rep coding region;
   (b) an AAV cap coding region; and
   (c) a nucleotide sequence comprising a polyadenylation signal situated 3' of an AAV p5 promoter and 5' of an AAV rep gene start codon.

6. The host cell of claim 5, wherein the polyadenylation signal is a globin polyadenylation signal comprising SEQ ID NO:8.

7. A host cell comprising an AAV helper function vector, said AAV helper function vector comprising an AAV rep coding region, wherein the rep coding region is under the control of an inducible promoter that expresses an amount of rep RNA that is substantially less than an amount expressed from an AAV p5 promoter.

8. The host cell of claim 7, wherein the host cell further comprises an AAV cap coding region.

9. A host cell comprising an AAV helper function vector, said AAV helper function vector comprising an AAV rep coding region, said rep coding region comprising a nucleotide sequence coding for long forms of Rep protein and short forms of Rep protein, wherein the rep coding region is regulated by an inducible promoter such that the host cell produces greater quantities of the short forms of Rep protein than of the long forms of Rep protein.

10. The host cell of claim 9, wherein the host cell further comprises an AAV cap coding region.

11. A nucleic acid molecule encoding AAV helper functions, said molecule comprising:

(a) an AAV rep coding region;
   (b) an AAV cap coding region; and
   (c) a nucleotide sequence comprising a polyadenylation signal situated 3' of an AAV p5 promoter and 5' of an AAV rep gene start codon.

12. The nucleic acid molecule of claim 11, wherein the polyadenylation signal is a globin polyadenylation signal comprising SEQ ID NO:8.

13. The nucleic acid molecule of claim 12, wherein said globin polyadenylation signal is inserted between base pairs −8 and −7 relative to the AAV rep gene start codon.

* * * * *